US00PP14095P29

(12) United States Plant Patent
Hoogendoorn

(10) Patent No.: US PP14,095 P2
(45) Date of Patent: Aug. 26, 2003

(54) ALSTROEMERIA PLANT NAMED 'STAPRIRANGE'

(75) Inventor: Cornelis Arie Hoogendoorn, Nieuwkoop (NL)

(73) Assignee: Van Zanten Plants B.V., Hillegom (NL)

( * ) Notice: Subject to any disclaimer, the term of this patent is extended or adjusted under 35 U.S.C. 154(b) by 0 days.

(21) Appl. No.: 10/200,309

(22) Filed: Jul. 22, 2002

(51) Int. Cl.[7] ..... A01H 5/00
(52) U.S. Cl. ..... Plt./309
(58) Field of Search ..... Plt./309

(56) References Cited

U.S. PATENT DOCUMENTS

PP11,692 P * 12/2000 van Andel ..... Plt./309

OTHER PUBLICATIONS

UPOV ROM GTITM Computer Database, GTI JOUVE Retrieval Software 2002/06, citation(s) for 'Staprirange'.* http://www.princesslilies.nl/Ella.htm.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Alstroemeria plant named 'Staprirange', characterized by its compact and uniform plant growth habit; freely branching habit; freely flowering habit; and light red and yellow-colored flowers with dark purple-colored spots and stripes.

1 Drawing Sheet

CROSS REFERENCE TO RELATED APPLICATIONS

The present application is related to copending U.S. Plant patent application Ser. No. 10/200,309 and 10/200,310.

Botanical classification cultivar designation: Alstroemeria hybrida cultivar Staprirange.

BACKGROUND OF THE INVENTION

The present Invention relates to a new and distinct cultivar of Alstroemeria plant, botanically known as Alstroemeria hybrida, commercially used as a flowering potted Alstroemeria, and hereinafter referred to by the name 'Staprirange'.

The new Alstroemeria is a product of a planned breeding program conducted by the Inventor in Aalsmeer, The Netherlands. The objective of the breeding program was to develop new flowering potted Alstroemeria cultivars with compact and uniform plant growth habit and attractive flower colors.

The new Alstroemeria originated from a cross made by the Inventor in April, 1994 in Aalsmeer, The Netherlands, of a proprietary Alstroemeria hybrida selection identified as 88D1240-2, not patented, as the female, or seed, parent with a proprietary Alstroemeria hybrida selection identified as 86F679-1, not patented, as the male, or pollen, parent. The new Alstroemeria was discovered and selected by the Inventor as a single flowering plant within the progeny of the stated cross in a controlled environment in Aalsmeer, The Netherlands in June, 1995. The selection of this new Alstroemeria was based on its compact plant growth habit and attractive flower coloration.

Asexual reproduction of the new cultivar by root divisions taken in a controlled environment in Aalsmeer, The Netherlands, since June, 1995, has shown that the unique features of this new Alstroemeria are stable and reproduced true to type in successive generations of asexual propagation.

SUMMARY OF THE INVENTION

Plants of the cultivar Staprirange have not been observed under all possible environmental conditions. The phenotype may vary somewhat with variations in environment such as temperature and light intensity without, however, any variance in genotype.

The following traits have been repeatedly observed and are determined to be the unique characteristics of 'Staprirange'. These characteristics in combination distinguish 'Staprirange' as a new and distinct cultivar:

1. Compact and uniform plant growth habit.
2. Freely branching habit, bushy appearance.
3. Freely flowering habit.
4. Light red and yellow-colored flowers with dark purple-colored spots and stripes.

Plants of the new Alstroemeria are most similar to plants of the parent selections. However, plants of the new Alstroemeria differ from plants of the parents in flower coloration as plants of the female parent have purple-colored flowers and plants of the male parent have orange-colored flowers. In addition, plants of the new Alstroemeria are more compact than plants of the male parent.

Plants of the new Alstroemeria differ from plants of the cultivar Stapriley, disclosed in U.S. Plant patent application Ser. No. 10/300,310, and the cultivar Staprivane, disclosed in U.S. Plant patent application Ser. No. 10/200,316, primarily in flower coloration.

Plants of the new Alstroemeria can be compared to plants of the cultivar Staprivina, disclosed in U.S. Plant Pat. No. 11,692. In side-by-side comparisons conducted in Rijsenhout, The Netherlands, plants of the new Alstroemeria differed primarily from plants of the cultivar Staprivina in flower coloration as plants of the cultivar Staprivina had salmon orange-colored flowers.

BRIEF DESCRIPTION OF THE PHOTOGRAPH

The accompanying colored photograph illustrates the overall appearance of the new Alstroemeria, showing the colors as true as it is reasonably possible to obtain in colored reproductions of this type. Colors in the photograph may differ slightly from the color values cited in the detailed botanical description which accurately describe the colors of the new Alstroemeria. The photograph comprises a side perspective view of a typical flowering plant of 'Staprirange' grown in a container.

DETAILED BOTANICAL DESCRIPTION

The aforementioned photograph, following observations and measurements describe plants of the new Alstroemeria grown in Rijsenhout, The Netherlands in a glass-covered greenhouse in 15-cm containers. During the production of the plants, day temperatures ranged from 10 to 15° C. and night temperatures ranged from 5 to 10° C. Plants used for the photograph and description were about four months from planting root divisions. The photograph and the description were taken during October and November, 2001.

Color references are made to The Royal Horticultural Society Colour Chart, 1995 Edition, except where general terms of ordinary dictionary significance are used.

Botanical classification: Alstroemeria hybrida cultivar Staprirange.

Parentage:

*Female parent*.—Proprietary Alstroemeria hybrida selection identified as 88D1240-2, not patented.

*Male parent*.—Proprietary selection of Alstroemeria hybrida identified as 86F679-1, not patented.

Propagation:

*Type*.—By root divisions.

*Root description*.—Fibrous, fleshy; white, close to 155D, in color.

*Rooting habit*.—Freely branching.

*Rhizomes*.—Shape: Elongate; rounded. Length: About 10 to 30 cm. Diameter: About 0.3 to 1 cm. Texture: Smooth. Color: Close to 155D.

Plant description:

*Plant habit*.—Compact and uniform plant growth habit; upright and outwardly spreading. Freely basal branching, about 15 to 20 lateral branches per plant; bushy appearance.

*Time from planting to flowering*.—About 80 to 90 days.

*Plant height*.—About 20 to 25 cm.

*Plant diameter* (*spread*).—About 30 to 40 cm.

*Lateral branch description*.—Aspect: Erect to outwardly arching. Length: About 12 to 21 cm. Diameter: About 4 to 5 mm. Internode length: About 5 to 10 mm. Strength: Strong. Texture: Glabrous. Color: Close to 144B.

*Foliage description*.—Leaves asymmetrical; sessile. Length: About 8 to 9.5 cm. Width: About 2 to 2.8 cm. Shape: Narrowly ovate. Apex: Acute. Base: Attenuate. Margin: Entire. Texture, upper and lower surfaces: Glabrous. Venation pattern: Parallel. Color: Young and fully developed foliage, upper surface: Close to 137A; slightly glossy. Young and fully developed foliage, lower surface: Close to 137B to 137C. Venation: Upper surface, close to 137A; lower surface, close to 137B to 137C.

Flower description:

*Flower type and habit*.—Single cup-shaped flowers arranged in compound umbels. Perianth segments separate. Freely and continuously flowering. Flowers not persistent.

*Natural flowering season*.—Flowering continuous during the spring in The Netherlands.

*Fragrance*.—None detected.

*Flower longevity on the plant*.—About four weeks.

*Flower longevity as a cut flower*.—About 18 to 20 days.

*Flower buds* (*showing color*).—Length: About 2.5 to 4 cm. Diameter: About 1 to 1.5 cm. Shape: Roughly ovoid. Color: Close to 46D.

*Umbel length*.—About 7 to 9 cm.

*Umbel diameter*.—About 10 to 13 cm.

*Number of flowers per umbel*.—About 3 to 20.

*Flower length*.—About 6.5 to 7.5 cm.

*Flower diameter*.—5.5 to 6.3 cm.

*Flower depth*.—About 5.5 to 6 cm.

*Perianth*.—Arrangement: Six arranged in two whorls, each whorl with two lateral and one median segments. Size: Inner perianth: Length: Laterals, about 5.5 to 6 cm; median, 5 to 5.5 cm. Width, laterals and median: About 1.7 to 2.3 cm. Outer perianth: Length: Laterals, about 5.2 to 5.8 cm; median, about 5.5 to 6 cm. Width: Laterals, about 2.6 to 3.3 cm; median, about 2.7 to 3.3 cm. Shape: Inner perianth, all segments: Oblanceolate. Outer perianth, all segments: Obovate. Apex: Inner perianth, all segments: Acute. Outer perianth, all segments: Emarginate to cordate. Base, inner and outer perianths, all segments: Attenuate. Margin, inner and outer perianths, all segments: Entire. Texture, inner and outer perianths, all segments: Smooth, glabrous; velvety. Color: Inner perianth: When opening and fully opened, upper surface: Laterals: Towards apex, close to 46C to 46D; center and towards base, close to 9A; spots and stripes, close to 187A. Median: Close to 46C; towards base, close to 34B; spots and stripes, close to 187A. When opening and fully opened, lower surface: Laterals: Towards apex, close to 46D; center and towards base, close to 9A. Median: Close to 46D. Outer perianth: When opening and fully opened, upper surface, laterals and median: Close to 46C; towards base, 46D. When opening and fully opened, lower surface: Laterals: Close to 46D. Median: Close to 46C to 46D.

*Pedicels*.—Length: About 3 to 8 mm. Diameter: About 2 to 3 mm. Strength: Strong. Angle: About 30 to 60° from vertical. Texture: Smooth, glabrous. Color: Close to 144A.

*Reproductive organs*.—Stamens: Quantity per flower: Six. Anther shape: Elliptical. Anther length: About 8.5 mm. Anther diameter: About 3 mm. Anther color: Close to 178B. Pollen amount: Scarce. Pollen color: Brownish. Pistils: Quantity per flower: One. Style length: About 4 to 4.5 cm. Style color: Red. Ovary color: Close to 144A.

*Fruit*.—Shape: Globular. Color: Brown.

Disease/pest resistance: Plants of the new Alstroemeria have not been observed to be resistant to pathogens and pests common to Alstroemerias.

Temperature tolerance: Plants of the new Alstroemeria have been observed to tolerate temperatures from −5 to 40° C.

Garden performance: Plants of the new Alstroemeria have been observed to be very tolerant to wind and rain and maintain good form and substance for about three months.

It is claimed:

1. A new and distinct cultivar of Alstroemeria plant named 'Staprirange', as illustrated and described.

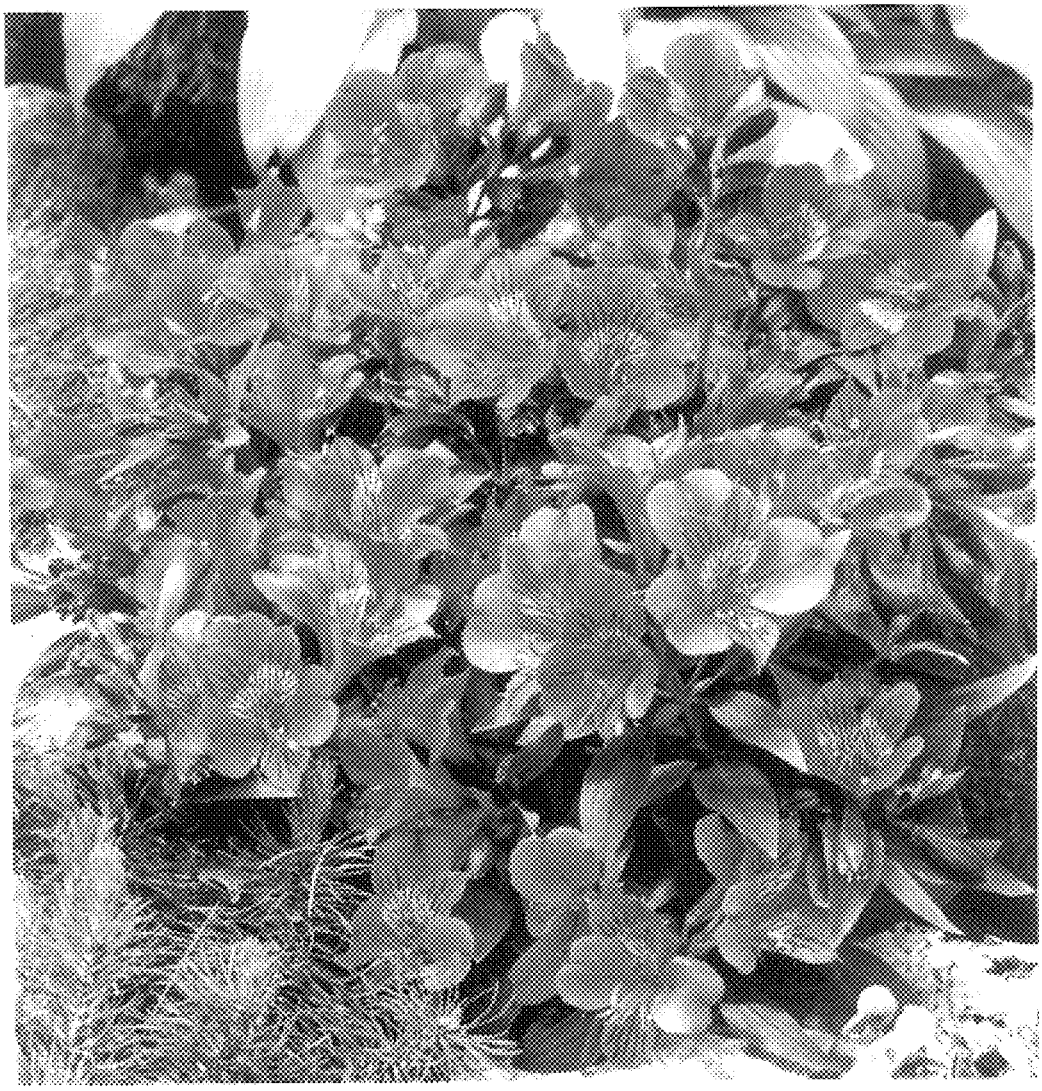

* * * * *